United States Patent [19]
Hudlicky et al.

[11] Patent Number: 5,627,280
[45] Date of Patent: May 6, 1997

US005627280A

[54] SYNTHESIS OF (+)-PANCRATISTATIN

[75] Inventors: Tomas Hudlicky, Blacksburg, Va.; Xinrong Tian, Beising, China; Kurt Konigsberger, Oberndorf, Austria

[73] Assignee: Virginia Tech Intellectual Properties, Inc., Blacksburg, Va.

[21] Appl. No.: 389,477

[22] Filed: Feb. 16, 1995

[51] Int. Cl.$^6$ .................................................. C07D 491/056
[52] U.S. Cl. .................................................. 546/65
[58] Field of Search .................................................. 546/65

[56] References Cited

PUBLICATIONS

Tian, Xinrong et al. (Mar. 1995) *Journal of the American Chemical Society* 117(12): 3643–3644.

*Primary Examiner*—Ba K. Trinh

[57] ABSTRACT

This is described an improved process for the asymetric synthesis of (+)-Pancratistatin utilizing aziridines as the starting materials.

11 Claims, No Drawings

SYNTHESIS OF (+)-PANCRATISTATIN

FIELD OF THE INVENTION

This invention relates to a method for the asymmetric synthesis of (+)-pancratistatin.

BACKGROUND OF THE INVENTION

Pancratistatin 1, a member of the Amaryllidaceae group of alkaloids, originates from plants used in herbal folk medicine as long ago as ancient Grecian times)[1,2] Structures of pancratistatin and its congeners have been elucidated by Pettit;[3] some have been synthesized,[4] although to date only one synthesis of racemic pancratistatin, by Danishefsky, has been reported.[5] This synthesis is not satisfactory for commercial scale up because it involves at least 26 steps, is racemic, and involves a large number of functional group manipulations. Approaches to pancratistatin and lycoricidine (a congener of pancratistatin) are known in the literature.[6] Pancratistatin exhibits promising antimitotic activities associated with other Amaryllidaceae alkaloids as well.[1,7] The established spectrum of biological activity of pancratistatin includes inhibition of protein synthesis and antineoplastic activities in ovarian sarcoma and lymphatic leukemia.[2] Its natural abundance is low (0.039% of the dry weight of ground roots of *Pancratium littorale*),[2] and the completion of biological screening would benefit from an efficient synthesis of this compound and closely related compounds.

Despite the desirability to synthesize pancratistatin and related compounds, efficient methods have heretofore been unavailable. Particularly, there has been no previous disclosure of an asymetric synthetic approach for (+)-pancratistatin. Therefore, it is an object of the present invention to provide a general method for the synthesis of pancratistatin and related compounds.

It is a further object of the present invention to provide an asymetric method for synthesis of pancratistatin, preferably by a method which can yield the product in a minimum number of steps.

These and other objects of the present invention will become apparent upon review of the following specification and claims appended thereto.

SUMMARY OF THE INVENTION

In accordance with the foregoing objectives, there is provided by the present invention a process for the synthesis of pancratistatin comprising:

a) providing an aziridine of the formula:

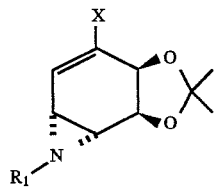
(8)

wherein:

X is H, halogen or CN (preferably X is H or halogen); and $R_1$ is a carbobenzyloxy group (CBZ) or tosyl (preferably $R_1$ is tosyl);

b) adding to the aziridine (8) an amide of the formula:

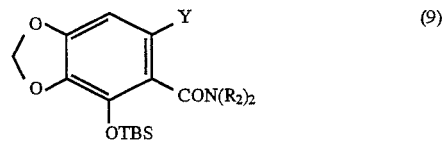
(9)

wherein:

Y is Li or Cu; and $R_2$ is methyl, ethyl or alkyl of C1-C5;

under appropriate conditions to yield an amide of the formula:

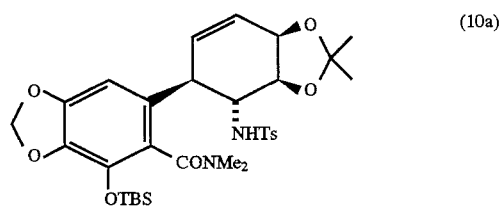
(10a)

c) acylating the amide product to Step b) with $(BOC)_2O$ to yield a compound of the formula:

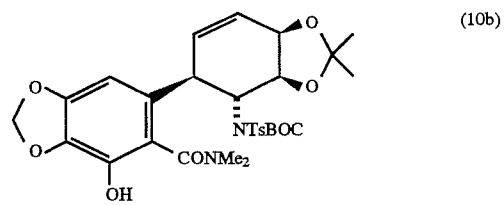
(10b)

d) detosylating (10b) to yield a dimethylamide of the formula:

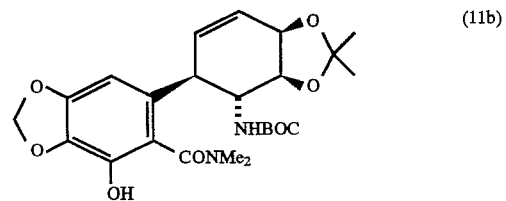
(11b)

e) reducing the dimethylamide (11b) to yield an aldehyde which can be further converted to a methyl ester of the formula:

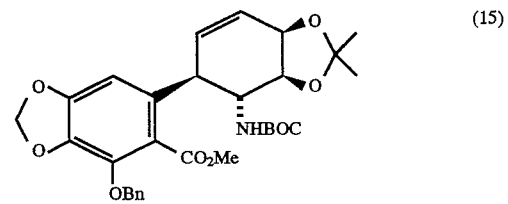
(15)

f) deprotecting the methyl ester and subjecting the deprotected compound to epoxidation to yield an epoxide of the formula:

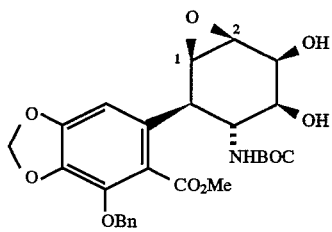

(16)

and;

g) opening the epoxide of Step f) with an appropriate nucleophile to yield pancratistatin (1).

In a preferred embodiment the conditions and reactions for each step in the synthesis are as noted in Scheme 1 hereof.

DETAILED DESCRIPTION OF THE PREFERRED EMBODIMENTS OF THE INVENTION

Although other approaches to pancratistatin have been suggested as noted above, the present invention relates to recognizing the configurational similarity between 1 and both D-chiro-inositol (3)[8] and conduramine A-1 (4),[9] as well as lycoricidine (5).[10]

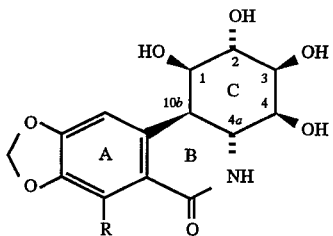

1 R = OH, Pancratistatin
2 R = H, Deoxypancratistatin

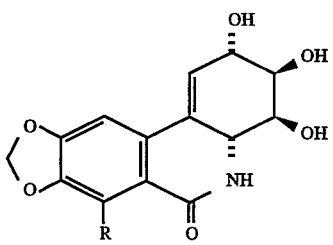

5 R = H, Lycoricidine
6 R = OH, Narciclasine

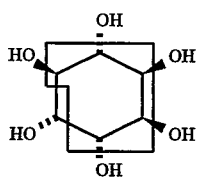

3 D-chiro-Inositol

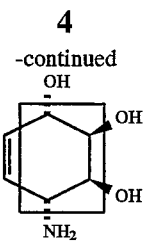

4 Conduramine A-1

All three of these compounds yielded to efficient syntheses in our laboratories starting with the protected diene diol 7, which contains the cis-diol unit common to all of the compounds. The trans-diol unit in 1 introduced via epoxide hydrolysis as demonstrated in the synthesis of D-chiro-inositol,[8] and the anti-disposition of hydroxyl and amino groups in pancratistatin, lycoricidine, and conduramine A-1 would be expected to result from the directing effect imposed by the protected cis-diol in 7. Diol 7, now also commercially available,[11a] is prepared by whole-cell oxidation of bromobenzene with *Pseudomonas putida* 39/D.[11b,c] The pivotal issue of synthetic design for the title compound therefore reduced to a method of attachment of the aryl moiety to C-10b in a stereocontrolled fashion.

The present approach to the problem of attaching the aryl, focused on the potential receptiveness of vinylaziridines 8 toward organometallic reagents derived from amide 9, Scheme 1. The synthesis of aziridines like compound 8 is disclosed in commonly owned US patent application Ser. No. 08/261,586 filed Jun. 17, 1994, the disclosure of any patents issuing thereon being incorporated herein by reference. Further disclosure regarding these compounds and their use in synthesizing disaccharides is provided in T. Hudlicky, et al, *Journ. Am. Chem. Soc.*, Vol. 116, No. 12, p. 5108–5115 (1994). Tosylaziridine 8a was generated according to the procedure of Evans,[12] and was subsequently reduced to 8b using $Bu_3SnH$/AIBN, THF, 78%. A preliminary study of the general tendencies of such a system toward $S_N2$ or $S_N2'$ opening with organometallic reagents was undertaken for the parallel series of aziridines 8a and 8b, and the results were compared to those for the corresponding oxiranes.[13] Conditions have been developed to furnish either $S_N2$ or $S_N2'$ opening. We found that higher-order cyanocuprate[14] afforded exclusively the desired $S_N2$-opening of 8b in spite of the shielding of the β-face by the acetonide. The aziridines discussed herein have previously been described in commonly owned U.S. Ser. No 08/261,586 filed Jun. 17, 1994, the disclosure of which is incorporated herein by reference.

Amide 9 was subjected to ortho-metallation below −90° C. by means of Snieckus' protocol[15] and converted in situ to the lithium cyanocuprate species $Ar_2Cu(CN)Li_2$,[14] whose addition to 8b produced cleanly the tosylamide 10a (75%). This compound was formed almost exclusively as one atropisomer (vide NMR and TLC), which slowly equilibrated at room temperature to its more stable form (presumably the α-form-atropisomers as shown for 11a). Having reached this point, the inventors faced additional problems associated with the fact that the transamidation procedure reported by Heathcock for a model system [6c] as applied to amide 10c[16], did not yield positive results because of the greatly enhanced acidity of the C-10b proton and concomitant epimerization resulting from the treatment of 10c with s-BuLi at low temperature. Additionally, attempts to functionalize the olefin in 10a failed as a consequence of the hindrance imposed on the α-face by the dimethylamide moiety. Finally, the ortho-disubstituted dimethylamide did not yield to hydrolysis even under conditions detrimental to the oxygenation of the C-ring. Applicants overcame the above problems at the expense of reduced efficiency, by acylation of 10a to 10b with (BOC)$_2$O (68%) and reduction of the tosylamide at this stage (Na/anthracene/DME, 82%).[17] With this particular reagent, the α-atropisomer underwent smooth detosylation and desilylation to furnish 11b, whereas the β-atropisomer gave only detosylation product 11a, which was isolated and subjected to TBAF treatment to afford 11b (93%). Reduction of the dimethylamide was modified sodium bis(methoxyethoxy)aluminum hydride to aldehyde 12 (72%)[18] and protection of the phenol afforded 13 (83%), which was oxidized (NaClO$_2$, KH$_2$PO$_4$, 2-methyl-2-butene, t-BuOH, H$_2$O)[19] to acid 14 and converted to methyl ester 15 in 98% yield. Again at this point in the synthetic process, the inventors faced difficulties associated with their attempts to epoxidize this methyl ester to furnish the α-epoxide, which attempts failed under a variety of conditions, again as a result of the atropisomerism and the effective blocking of the α-face of the molecule by the methyl ester and BOC groups. Deprotection (HOAc/THF/H$_2$O, 2:1:1, 73%) and VO(acac)$_2$-catalyzed t-BuOOH epoxidation[20] on the β-face, directed by the free hydroxy, afforded the β-epoxide 16 (53%). In this epoxide, only the C-2 site is available to diaxial opening by nucleophiles. The nearly neutral conditions (H$_2$O, sodium benzoate (cat.), 100° C., 6 days) adapted from the D-chiro-inositol preparation accomplished, in addition to the stereospecific epoxide opening, a quite remarkable series of events including thermal cleavage of the BOC group, cyclization to the lactam, as well as debenzylation to the title compound in 51% yield. This reaction led in 48 h to benzyl protected pancratistatin 17 (80%), which was then quantitatively hydrogenated to 1. Thus the total synthesis of (+)-pancratistatin, found identical to the natural material ($^1$H-NMR, R$_f$=0.40, CHCl$_3$/CH$_3$OH, 4:1), has been achieved in no more than 13 steps and with an overall yield of 2%.

SCHEME 1

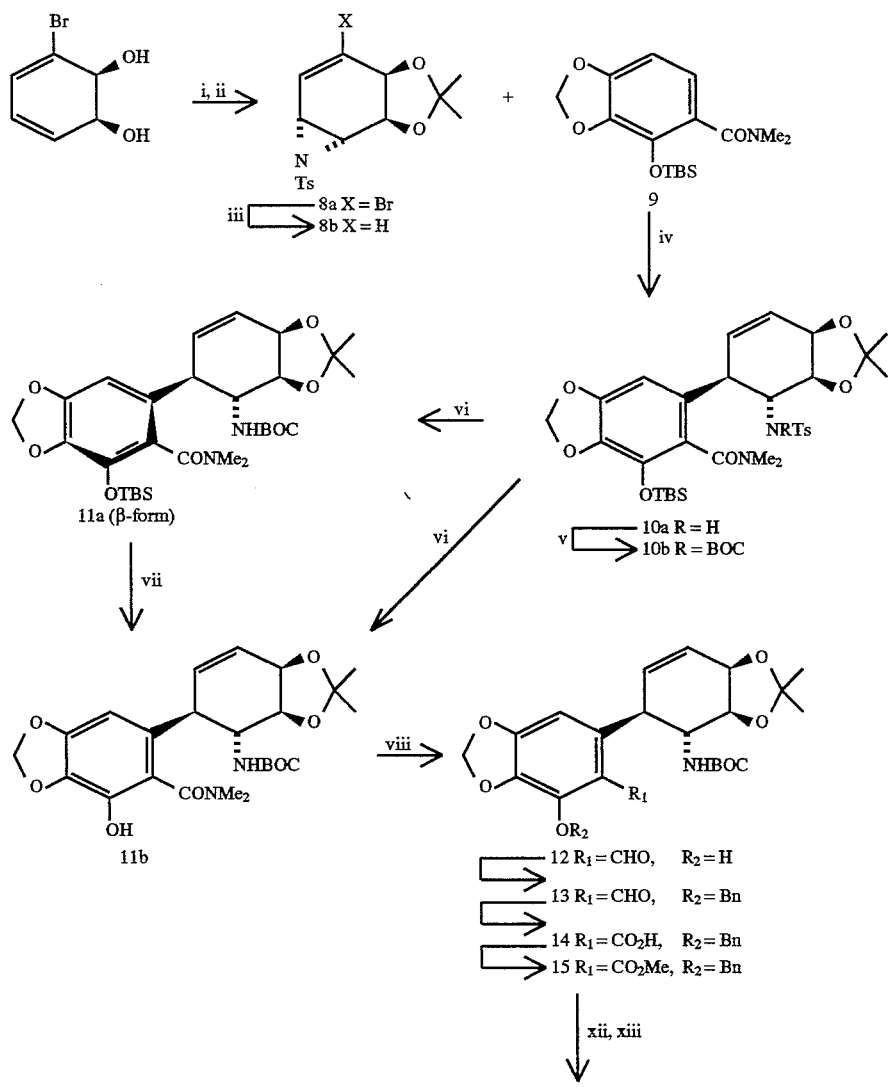

-continued
SCHEME 1

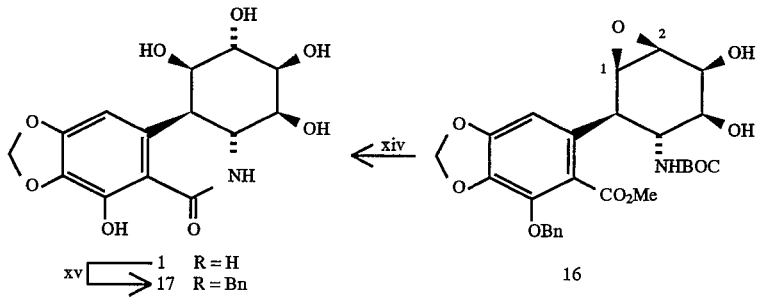

Scheme 1a

*(i) DMP, p-TsOH, CH$_2$Cl$_2$; (ii) PhI=NTs, Cu(acac)$_2$, CH$_3$CN; (iii) Bu$_3$SnH, AIBN, THF; (iv) s-BuLi, TMEDA, THF, −90° C.; CuCN, −78° C. to −20° C.; 8b, −78° C. to rt; (v) s-BuLi, (BOC)$_2$O, THF; (vi) Na/anthracene, DME, −78° C.; (vii) TBAF, THF; (viii) SMEAH-morpholine, −45° C., THF; (ix) BnBr, K$_2$CO$_3$, DMF; (x) NaClO$_2$, KH$_2$PO$_4$, 2-methyl-2-butene, t-BuOH, H$_2$O; (xi) CH$_2$N$_2$; (xii) HOAc-THF-H$_2$O, 60° C.; (xiii) t-BuOOH, VO(acac)$_2$, benzene, 60° C.; (xiv) H$_2$O, BzONa (cat.), 100° C.; (xv) H$_2$, Pd(OH)$_2$/C, EtOAc.

In summary, this synthesis demonstrated several anomalies of modern synthetic chemistry. Of the 13 steps, more than half of the effort has been expended on the manipulation of the benzamide and the tosylamide moieties required for the coupling. Although eminently useful in ortho-metallation, the benzamide and the methods of its subsequent transformations have been found incompatible with the use of sensitive functional groups. Efforts are now under way to eliminate the use of both of these functionalities and to furnish a shorter synthesis of pancratistatin in a practical fashion. These endeavors will be readily understandable to those skilled in the art based on the present teachings.

The procedures, reactants and reaction conditions for the above reactions will be readily understood by one of ordinary skill in the art. The following examples illustrate the invention. It is understood, however, that these examples are not to be interpreted as limiting the scope of the invention.

EXAMPLES

EXAMPLE 1

N,N-Dimethyl-4-(tert-butyldimethylsilyloxy)-1,3-benzodioxole-5-carboxamide (9)

t-Butyldimethylsilyl chloride (4.02 g, 26.67 mmol) in CH$_2$Cl$_2$ (25 ml) was added to a solution of N,N-dimethyl-4-hydroxy-1,3-benzodioxole-5-carboxamide (5) (4.49 g, 20.5 mmol) and imidazole (3.63 g, 53.3 mmol) in CH$_2$Cl$_2$ (25 ml). The solution was stirred for 3 h at rt, during which time a white solid precipitated. The mixture was washed with brine, dried over MgSO$_4$ and concentrated. Chromatography on silica (hexane/ethyl acetate, 1:1) afforded 9 (5.44 g, 82%) as a crystalline solid. $^1$H NMR (270 MHz, CDCl$_3$) ε 6.75 (d, J=8.0 Hz, 1H), 6.50 (d, J=8.0 Hz, 1H), 5.92 (s, 2H), 3.03 (s, 3H), 2.87 (s, 3H), 0.94 (s, 9H), 0.16 (bs, 6H). $^{13}$C NMR (100 MHz, CDCl$_3$) ε 168.9 (C), 149.3 (C), 137.0 (C), 135.5 (C), 124.9 (C), 121.4 (CH), 102.8 (CH), 101.0 (CH$_2$), 38.2 (CH$_3$), 34.9 (CH$_3$), 25.4 (3CH$_3$), 18.1 (C), −4.6 (2CH$_3$).

EXAMPLE 2

N,N-Dimethyl-4-(tert-butyldimethylsilyloxy)-6-[(1R,4R,5S,6R)-4,5-isopropylidenedioxy-6-(4-methylphenylsulfonylamino)-2-cyclohexen-1-yl]-1,3-benzodioxole-5-carboxamide (10a).

s-BuLi in hexane (1.28M, 40 ml) was added to a solution of tetra methylethylenediamine (TMEDA) (7.68 ml) in THF (160 ml) at −78° C., the yellow mixture was stirred for 10 min before cooling to −90° C., and a solution of amide 9 (14.71 g, 45.4 mmol) in THF (60 ml) was added precooled by cannula. The resulting deep red solution was stirred at −90° C. for 1.5 h and transferred to a round bottom flask charged with CuCN (2.08 g, 22.75 mmol). The tannish mixture was warmed to −20° C. furnishing a dark purple solution, which was recooled to −78° C., and a solution of vinylaziridine 8b (as made per the disclosure of U.S. Ser. No. 08/261,586 filed Jun. 17, 1994 and incorporated herein) (4.81 g, 14.96 mmol) in THF (40 ml) was added, followed by BF$_3$.Et$_2$O (2.8 ml). The reaction mixture was then warmed to rt over 8 h and saturated aqueous NH$_4$Cl solution (10 ml, containing NH$_4$OH, pH 8) was added. The mixture was stirred at rt for 30 min, the organic layer was separated and the aqueous layer was extracted with EtOAc (3×25 ml). The combined organic layers were dried over Na$_2$SO$_4$ and concentrated in vacuo. The residue was chromatographed on silica gel eluting with hexane/EtOAc (3:2) (for one atropisomer) followed by hexane/EtOAc (2:3) (for the other atropisomer) to give 6.88 g (75%) of 10a as a glassy solid. $^1$H NMR (270 MHz, CDCl$_3$) ε 7.62 (d, J=8.1 Hz, 2H), 7.09 (d, J=8.1 Hz, 2H), 6.26 (s, 1H), 5.9–6.05 (m, 3H), 5.79 (d, J=9.8 Hz, 1H), 4.58 (m, 1H), 3.99 (dd, J=9.5, 6.2 Hz, 1H), 3.34 (td, J=10.1, 6.4 Hz, 1H), 3.10 (d, J=10.1 Hz, 1H), 3.08 (s, 3H), 2.87 (s, 3H), 2.36 (s, 3H), 1.45 (s, 3H) 1.29 (s, 3H), 0.97 (s, 9H), 0.27 (s, 3H), 0.23 (s, 3H). $^{13}$C NMR (68 MHz, CDCl$_3$)ε 169.08 (C), 149.68 (C), 141.14 (C), 139.89 (C), 135.93 (C), 134.58 (CH), 132.21 (C), 128.25 (2×CH), 127.00 (2×CH), 125.16 (CH), 123.66 (C), 109.28 (C), 101.66 (CH), 101.11 (C), 79.11 (CH), 72.53 (CH), 58.59 (CH), 42.91 (CH), 37.77 (CH), 34.90 (CH), 27.68 (CH$_3$), 25.80 (CH$_3$), 25.44 (3×CH$_3$), 21.94 (CH$_3$), 17.94 (C), −4.57 (2×CH$_3$).

EXAMPLE 3

N,N-Dimethyl-4-(tert-butyldimethylsilyloxy)-6-{(1R,4R,5S,6R)-6-[N-(tert-butyloxycarbonyl)-N-(4-methylphenylsulfonyl)amino]-4,5-isopropylidenedioxy-2-cyclohexen-1-yl}-1,3-benzodioxole-5-carboxamide (10b).

s-BuLi in hexane (1.28M, 7.02 ml) was added to a solution of tosylamide 10a (5.04 g, 8.17 mmol) in THF (25 ml) at 0° C. The mixture was stirred at 0° C. for 15 min and di-tert-butyl dicarbonate (7.13 g, 32.6 mmol) was added. After refluxing for 4 days the reaction mixture was quenched with 10 ml of brine, the organic layer was separated and the aqueous phase was extracted with EtOAc (3×20 ml). The combined organic layers were dried over $Na_2SO_4$ and concentrated in vacuo. Chromatography of the residue (silica, hexane/ethyl acetate, 3:2) afforded 4.14 g (68%) of a mixture of atropisomers, 10b. For the α-form, $^1$H NMR (270 MHz, $CDCl_3$) ε 7.52 (d, J=8.1 Hz, 2H), 7.10 (d, J=8.1 Hz, 2H), 6.60 (s, 1H), 5.87 (m, 4H), 5.70 (m, 1H), 5.06 (dd, J=9.7, 5.8 Hz, 1H), 4.76 (t, J=10.8 Hz, 1H), 4.69 (t, J=5.1 Hz, 1H), 4.20 (d, J=10.0 Hz, 1H), 3.06 (s, 3H), 2.83 (s, 3H), 2.41 (s, 3H), 1.69 (s, 3H), 1.54 (s, 3H), 1.25 (s, 9H), 0.94 (s, 9H), 0.21 (s, 6H).

EXAMPLE 4

N,N-Diethyl-6-[(1R,4R,5S,6R)-6-amino-4,5-isopropylidenedioxy-2-cyclohexen-1-yl]-4-(ethoxymethoxy)-1,3-benzodioxole-5-carboxamide (10c).

To a solution of N,N-diethyl-4-(ethoxymethoxy)-6-[4,5-isopropylidenedioxy-6-(4-methylphenylsulfonylamino)-2-cyclohexen-1-yl]-1,3-benzodioxole-5-carboxamide (251 mg, 0.41 mmol) in methanol (3 ml) and THF (1 ml) were added $Na_2HPO_4$ (349 mg) and sodium amalgam (6%, 1.68 g). After stirring overnight at rt, additional $Na_2HPO_4$ (234 mg) and sodium amalgam (1.24 g) were added. Stirring was continued for 5 h, water (2 ml) was then added and the mixture was extracted with ethyl acetate (3×5 ml). The organic layer was dried over $Na_2SO_4$ and concentrated in vacuo. The residue was subjected to chromatography (silica, $CHCl_3/CH_3OH$, 13:1) to afford 39 mg (20%) of 10c. $^1$H NMR (270 MHz, $CDCl_3$) ε 6.47 (s, 1H), 6.01 (dt, J=10.2, 3.4 Hz, 1H), 5.97 (dd, J=5.7, 1.4 Hz, 2H), 5.76 (d, J=9.8 Hz, 1H), 5.31 (d, J=5.8 Hz, 1H), 5.27 (d, J=5.8 Hz, 1H), 4.62 (m, 1H), 4.07 (dd, J=9.5, 6.3 Hz, 1H), 3.73 (m, 3H), 3.20 (m, 1H), 3.03 (d, J=10.1 Hz, 1H), 2.95 (bs, 2H), 2.80 (t, J=9.8 H, 1H), 1.53 (s, 3H), 1.40 (s, 3H), 1.21 (m, 6H), 1.02 (t, J=7.1 Hz, 3H).

EXAMPLE 5

N,N-Dimethyl-6-[(1R,4R,5S,6R)-6-(tert-butyloxycarbonylamino)-4,5-isopropylidenedioxy-2-cyclohexen-1-yl]-4-hydroxy-1,3-benzodioxole-5-carboxamide (11b).

A solution of sodium anthracenide (ca. 0.6N) was added dropwise under Ar at −78° C. to a stirred solution of 10b (5.68 g, 7.62 mmol) in DME (30 ml), until a blue color persisted for 15 min. The reaction mixture was quenched with saturated $NH_4Cl$ solution (5 ml) and the solvent was removed in vacuo. The residue was taken up in ethyl acetate and filtered. Concentration and chromatography of the residue (silica, hexane/ethyl acetate, 2:3) gave 11a (2.81 g, 62% and 11b (0.75 g, 20%).

A solution of tetrabutylammonium fluoride in THF (1M, 9.8 mL) was added to a solution of 11a (2.81 g, 4.76 mmol) in THF (35 ml) at 0° C. The resulting brown solution was stirred at 0° C for 1.5 h, the solvent was removed in vacuo and the residue was chromatographed (silica, ethyl acetate) to furnish 2.11 g (93%) of 11b. 10a, $^1$H NMR (270 MHz, $CDCl_3$) ε 6.50 (s, 1H), 5.88 (m, 4H), 4.58 (m, 1H), 3.70~4.3 (m, 3H), 3.30 (m, 1H), 3.07 (s, 3H), 2.91 (s, 3H), 1.54 (s, 3H), 1.38 (s, 3H), 1.28 (s, 9H), 0.94 (s, 9H), 0.24 (s, 3H), 0.14 (s, 3H). 10b, $^1$H NMR (270 MHz, $CDCl_3$) ε 9.73 (bs, 1H), 6.39 (bs, 2H), 5.98 (d, J=9.6 Hz, 1H), 5.82 (d, J=5.6 Hz, 1H), 4.59 (t, J=4.2 Hz, 1H), 3.60~4.40 (m, 3H), 2.98~3.40 (m, 7H), 1.53 (s, 3H), 1.38 (s, 3H), 1.20 (s, 9H).

EXAMPLE 6

6-[(1R,4R,5S, 6R)-6-(tert-Butyloxycarbonylamino)-4,5-isopropylidenedioxy-2-cyclohexen-1-yl]-4-hydroxy-1,3-benzodioxole-5-carbaldehyde (12).

Morpholine-modified sodium bis(2-methoxyethoxy) aluminum hydride (SMEAH) in toluene (1.02 M, 20 ml) was added to a stirred solution of 11b (2.82 g) in THF (80 ml) at −45° C. After 9 h more SMEAH solution (9 ml) was added, and the mixture was stirred for another 22 h. The reaction was then quenched with saturated $NH_4Cl$ solution (10 ml) and brine (10 ml). The organic phase was separated and the aqueous layer was extracted with ethyl acetate (3×50 ml). Drying of the combined organic layers, concentration and chromatography of the residue gave 853 mg (72%, based on recovered 11b) of aldehyde 12 and 1.52 g of recovered starting material. $^1$H NMR (270 MHz, $CDCl_3$) ε 10.18 (s, 1H), 6.45 (s, 1H), 6.07 (bs, 3H), 5.93 (d, J=10.0 Hz, 1H), 4.68 (m, 2H), 4.50 (bs, 1H), 4.36 (bs, 1H), 3.31 (bs, 1H), 1.51 (s, 3H), 1.41 (s, 3H), 1.32 (s, 9H).

EXAMPLE 7

6-[(1R,4R,5S,6R)-6-(tert-Butyloxycarbonylamino)-4,5-isopropylidenedioxy-2-cyclohexen-1-yl]-4-(phenylmethoxy)-1,3-benzodioxole-5-carbaldehyde (13).

Benzyl bromide (0.351 ml) was added to a suspension of phenol 12 (853 mg, 1.97 mmol) and $K_2CO_3$ (544 mg, 3.94 mmol) in DMF (8 ml). The reaction mixture was stirred at rt for 4 h and then quenched with saturated $CuSO_4$ solution (5 ml) and brine (5 ml). The aqueous layer was extracted with ethyl acetate (3×15 ml), and the combined organic layers were dried over $Na_2SO_4$. Removal of the solvent and chromatography of the residue afforded 869 mg (83%) of 13. $^1$H NMR (270 MHz, $CDCl_3$) ε 10.38 (s, 1H), 7.37 (m, 5H), 6.63 (s, 1H), 6.02 (d, J=12.6 Hz, 2H), 6.00 (m, 1H), 5.82 (d, J=9.9 Hz, 1H), 5.34 (s, 2H), 4.83 (d, J=10.8 Hz, 1H), 4.65 (m, 2H), 4.06 (dd, J=10.3, 5.1 Hz, 1H), 3.71 (q, J=10.4 Hz, 1H), 1.54 (s, 3H), 1.40 (s, 3H), 1.23 (s, 9H). $^{13}$C NMR (68 MHz, $CDCl_3$) ε 192.83 (CHO), 155.54 (C), 153.82 (C), 145.59 (C), 140.88 (C), 136.30 (C), 135.69 (CH), 135.13 (C), 128.62 (2×CH), 128.50 (2×CH), 127.94 (CH), 124.10 (CH), 121.52 (C), 109.60 (C), 104.52 (CH), 101.85 ($CH_3$), 78.57 (C), 77.87 (CH), 74.58 (CH), 72.80 (CH), 56.48 (CH), 40.87 (CH), 28.15 (3×$CH_3$), 26.19 (2×$CH_3$).

EXAMPLE 8

Methyl 6-[(1R,4R,5S,6R)-6-(tert-butyloxycarbonylamino)-4,5-isopropylidenedioxy-2-cyclohexen-1-yl]-4-(phenylmethoxy)-1,3-benzodioxole-5-carboxylate (15).

Aldehyde 13 (507 mg, 0.97 mmol) was dissolved in t-BuOH (24 ml) and 2-methyl-2-butene (6.6 ml, 85% purity). A solution of sodium chlorite (1.18 g, 10.4 mmol) and potassium dihydrogen phosphate (1.07 g, 7.9 mmol) in $H_2O$ (10 ml) was added dropwise over a 10 min period. The yellow solution was stirred at rt overnight. Volatiles were removed under high vacuum, brine (3 ml) was added to the residue and extracted with ethyl acetate (4×20 ml). The extract containing the crude acid 14 was dried over $Na_2SO_4$ and treated with excess diazomethane. Removal of the solvent and chromatography (silica, hexane/ethyl acetate, 3:2) gave the methyl ester 15 (526 mg, 98%). $^1$H NMR (270 MHz, $CDCl_3$) ε 7.26~7.39 (m, 5H), 6.54 (s, 1H), 5.84~5.99 (4H, m), 5.21 (s, 2H), 4.94 (bs, 1H), 4.63 (t, J=4.4 Hz, 1H), 4.01 (bs, 1H), 3.79 (s, 3H), 3.73 (q, J=10.1 Hz, 1H), 3.36 (bs, 1H), 1.61 (s, 3H), 1.40 (s, 3H), 1.27 (s, 9H).

EXAMPLE 9

Methyl 6-[(1R,4R,5S,6R)-6-(tert-butyloxycarbonylamino)-4,5-dihydroxy-2-cyclohexen-1-yl]- 4-(phenylmethoxy)-1,3-benzodioxole-5-carboxylate.

Methyl ester 15 (488 mg, 0.88 mmol) was dissolved in a mixture of acetic acid, THF and $H_2O$ (2:1:1) (8 ml) and the solution was heated at 75° C. for 3 h. The solvent was removed in vacuo and the residue was subjected to chromatography (hexane/ethyl acetate, 1:4) to afford 324 mg of 4,5-diol as a white solid. $^1H$ NMR (270 MHz, $CDCl_3$), 7.27~7.40 (m, 5H), 6.61 (s, 1H), 6.15 (bs, 1H), 5.97 (m, 3H), 5.59 (d, J=9.1 Hz, 1H), 5.23 (AB, J=11.3 Hz, Δv=25.1 Hz, 2H), 4.83 (bs, 1H), 4.23 (t, J=3.3 Hz, 1H), 3.87 (m, 1H), 3.73 (s, 3H), 3.61 (m, 1H), 3.31 (bs, 1H), 3.29 (d, J=10.2 Hz, 1H), 1.38 (s, 9H). $^{13}C$ NMR (68 MHz, $CDCl_3$) ∈ 168.83 (C), 158.68 (C), 151.08 (C), 139.38 (C), 136.92 (C), 136.10 (C), 134.91 (C), 132.75 (CH), 128.40 (CH), 128.13 (CH), 127.80 (CH), 126.98 (CH), 120.88 (C), 103.60 (CH), 101.72 ($CH_2$), 80.03 (C), 74.86 (CH), 74.39 (CH), 66.68 (CH), 54.66 (CH), 52.50 ($CH_3$), 45.02 (CH), 28.29 (3×$CH_3$).

EXAMPLE 10

Methyl 6-[(1R,2R,3S, 4S,5S,6R)-2-(tert-butyloxycarbonylamino)-5,6-epoxy-3,4-dihydroxycyclohex-1-yl]-4-(phenylmethoxy)-1,3-benzodioxole-5-carboxylate (16).

t-Butylhydroperoxide in decane (5M, 0.45 ml) was added to a solution of methyl 6-[(1R,4R,5S,6R)-6-(tert-butyloxycarbonylamino)-4,5-dihydroxy-2-cyclohexen-1-yl]- 4-(phenylmethoxy)-1,3-benzodioxole-5-carboxylate (280 mg, 0.55 mmol) and vanadyl acetylacetonate (7 mg, 0.026 mmol) in benzene (10 ml). After stirring for 2 h at 60° C, the reaction mixture was concentrated under reduced pressure and subjected to chromatography (hexane/ethyl acetate, 1:5) to afford 129 mg (53%) of epoxide 16 and 42 mg of recovered starting material. $^1H$ NMR (270 MHz, $CDCl_3$) ∈ 7.27~7.40 (m, 5H), 7.04 (s, 1H), 5.99 (d, J=2.3 Hz, 2H), 5.68 (bd, J=7.3 Hz, 1H), 5.24 (AB, J=11.3 Hz, Δv=16.5 Hz, 2H), 4.28 (t, J=4.99 Hz, 1H), 3.83 (m, 4H), 3.35~3.46 (m, 3H), 3.07 (d, J=10.9 Hz, 1H), 1.33 (s, 9H).

EXAMPLE 11

Pancratistatin (1)

Method A. A suspension of epoxide 16 (109 mg, 0.21 mmol) and sodium benzoate (1 mg) in water (8 ml) was stirred at 100° C. for 6 days. The mixture was then concentrated and subjected to chromatography ($CHCl_3$/$CH_3OH$, 4:1) to afford 35 mg (51%) of pancratistatin. $^1H$ NMR (400 MHz, DMSO-$d_6$) ∈ 13.06 (s, 1H), 7.51 (s, 1H), 6.48 (s, 1H), 6.05 (d, J=1.0 Hz, 1H), 6.02 (d, J=1.0 Hz, 1H), 5.35 (bs, 1H), 5.04 (bs, 2H), 4.84 (bs, 1H), 4.27 (bs, 1H), 3.95 (bs, 1H), 3.84 (bs, 1H), 3.74 (m, 2H), 2.96 (d, J=11.5 Hz, 1H).

Method B. (1R,2S,3S,4S,4aR,10bR)-1,2,3,4-Tetrahydroxy-8,9-methylenedioxy-7-phenylmethoxy-1,3,4,4a,5,10b-hexahydro-1,3-dioxolo[4,5-j]phenanthridin-6-(2H)-one (17). Sodium benzoate (1 mg) was added to a suspension of epoxide 16 (51 mg, 0.096 mmol) in water (4 ml). The mixture was stirred at 100° C. for 48 h and then concentrated in vacuo. The residue was subjected to chromatography (silica, $CHCl_3$/$CH_3OH$, 10:1 TO 7:1) to furnish 32 mg (80%) of 17. $^1H$ NMR (270 MHz, $CDCl_3$), 7.53 (m, 2H), 7.33 (m, 3H), 6.87 (s, 1H), 6.68 (s, 1H), 6.06 (AB, J=0.8 Hz, Δv=17.1 Hz, 2H), 5.36 (d, J=4.0 Hz, 1H), 5.12 (m, 2H), 5.04 (d, J=6.5 Hz, 1H), 4.77 (d, J=7.6 Hz, 1H), 4.28 (m, 1H), 3.96 (q, J=3.2 Hz, 1H), 3.83 (m, 1H), 3.71 (m,1H), 3.57 (dd, J=12.4, 9.6 Hz, 1H), 2.88 (dd, J=12.4, 2.0 Hz, 1H). Pd(OH$_2$)/C (100 mg) was added to a suspension of 17 (13 mg, 0.031 mmol) in EtOAc (1 ml). The headspace was filled with $H_2$, the reaction mixture was stirred for 30 min and filtered through a short pad of silica which was subsequently rinsed with $CHCl_3$/$CH_3OH$ (4:1). The solvent was evaporated in vacuo to yield pancratistatin (10 mg, 99%).

The opening of a similar epoxide using benzoate and water has previously been described in commonly owned U.S. Ser. No. 07/974,057, incorporated herein by reference.

REFERENCES (1) Pettit, G. R.; Cragg, G. M.; Singh, S. B.; Duke, J. A.; Doubek, D. L. *J. Nat. Prod.* 1990, 53, 176.

(2) Pettit, G. R.; Gaddamidi, V.; Herald, D. L.; Singh, S. B.; Cragg, G. M.; Schmidt, J.; Boettner, F. E.; Williams, M.; Sagawa, Y. *J. Nat. Prod.* 1986, 49, 995.

(3) (a) Jiminez, A.; Sanchez, L.; Vazquez, D. *FEBS Lett.* 1975, 60,66. (b) Rivera, G. L.; Gosalbez, M. P.; Ballesta, J. P. G. *Biochem. Biophys. Res. Comm.* 1980, 94, 800. (c) Baez, A.; Vazquez, D. *Biochem. Biophys. Acta.* 1978, 518, 95.

(4) (a) Chida, N.; Ohtsuka, M.; Ogawa, S. *Tetrahedron Lett.* 1991, 32, 4525. (b) Paulsen, H.; Stubbe, M. *Liebigs Ann. Chem.* 1983, 535. (c) Paulsen, H.; Stubbe, M. *Tetrahedron Lett.* 1982, 23, 3171. (d) Ohta, S.; Kimoto, S. *Chem. Pharm. Bull.* 1976, 24, 2977. (e) Ohta, S.; Kimoto, S. *Tetrahedron Lett.* 1975, 2279. (f) Chida, N.; Ohtsuka, M.; Ogawa, S. *J. Org. Chem.* 1993, 58, 4441. (g) Johnson, C. R. "Synthesis of (+)- and (–)-lycoricidine via lipase resolution of conduramines", Abstr. of National Organic Symposium, Bozeman, MT, 1993. (h) Martin, S. F.; Tso, H. H. *Heterocycles,* 1993, 35, 85.

(5) Danishefsky, S.; Lee, J. Y. *J. Am. Chem. Soc.* 1989, 111, 4829.

(6) (a) Clark, R. D.; Souchet, M. *Tetrahedron Lett.* 1990, 31, 193. (b) Thompson, R. C.; Kallmerten, J. *J. Org. Chem.* 1990, 55, 6076. (c) Lopes, R. S. C.; Lopes, C. C.; Heathcock, C. H. *Tetrahedron Lett.* 1992, 33, 6775. (d) Angle, S. R.; Louie, M. S. *Tetrahedron Lett.* 1993, 34, 4751. (e) Doyle, T. J.; Hendrix, M.; Haseltine, *J. Tetrahedron Lett.* 1994, 35, 8295. (f) In addition to our efforts in this area, we are aware, by personal communication, of at least two additional approaches, those of Professors Gary Keck of the University of Utah, Carl Johnson of Wayne State University.

(7) (a) Baez, A.; Vazquez, D. *Biochem. Biophys. Acta* 1978, 518, 95. (b) Jiminez, A.; Santos, A.; Alonso, G.; Vazquez, D. *Biochem. Biophys. Acta* 1976, 425, 342. (c) Pettit, G. R.; Gaddamidi, V.; Cragg, G. M. *J. Nat. Prod.* 1984, 47, 1018.

(8) (a) Mandel, M.; Hudlicky, T. *J. Org. Chem.* 1993, 58, 2331. (b) Hudlicky, T.; Mandel, M.; Rouden, J.; Lee, R. S.; Bachmann, B.; Dudding, T.; Yost, K. Y.; Merola, J. S. *J. Chem. Soc., Perkin Trans. 1* 1994, 1553.

(9) (a) Hudlicky, T.; Olivo, H. F. *Tetrahedron Lett.* 1991, 32, 6077. (b) Hudlicky, T.; Luna, H.; Olivo, H.; Andersen, C.; Nugent, T.; Price, J. *J. Chem. Soc., Perkin Trans. 1* 1991, 2907.

(10) (a) Hudlicky, T.; Olivo, H. F.; *J. Am. Chem. Soc.* 1992, 114, 9694. (b) Hudlicky, T.; Olivo, H. F.; McKibben, B. *J. Am. Chem. Soc.* 1994, 116, 5108.

(11) (a) Available from Eastman Fine Chemical, Rochester, N.Y. and Genencor International, Inc. South San Francisco, Calif. (b) For laboratory scale fermentation see: Hudlicky, T.; Boros, E. E.; Boros, C. H. *Synthesis* 1992, 174. (c) Gibson, D. T.; Hensley, M.; Yosioka, H.; Mabry, T. *J. Biochemistry* 1970, 9, 1626.

(12) (a) For the preparation of PhI=NTs see: Yamada, Y.; Yamamoto, T.; Okawara, M. *Chem. Lett.* 1975, 361. (b) Evans, D. A.; Faul, M. M.; Bilodeau, M. T. *J. Org. Chem.* 1991, 56, 6744.

(13) (a) Hudlicky, T.; Tian, X.; Königsberger, K.; Rouden, J. *J. Org. Chem.* 1994, 59, 4037. (b) Hudlicky, T.; Reed, J. W. In *Comprehensive Organic Synthesis*; Trost, B. M.; Fleming, I., Eds.; Pergamon: Oxford, GB, 1991; Vol. 5, p 899. (c) Marshall, J. A. *Chem. Rev.* 1989, 89, 1503.

(14) Lipshutz, B. H.; Kozlowski, J.; Wilhelm, R. S. *J. Am. Chem. Soc.* 1982, 104, 2305.

(15) (a) Iwao, M.; Reed, J. N.; Snieckus, V. *J. Am. Chem. Soc.* 1982, 104, 5531. (b) Watanabe, M.; Sahara, M.; Kubo, M.; Furukawa, S.; Billedeau, R. J.; Snieckus, V. *J. Org. Chem.* 1984, 49, 742.

(16) Treatment of 10c (prepared in a similar fashion to 10a) with s-BuLi resulted in only epimerization at C-10b.

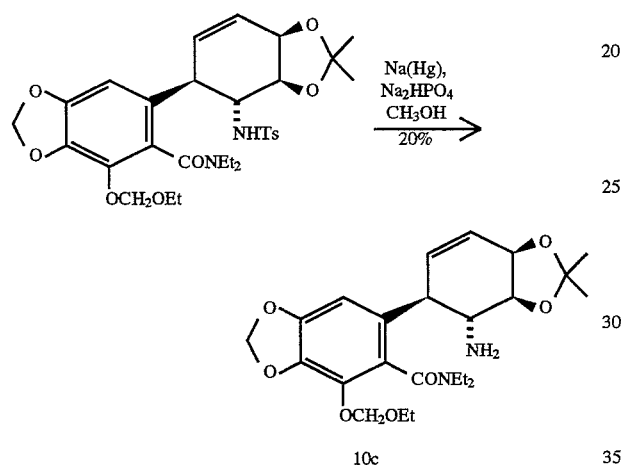

(17) Johnson, C. R.; Lavergne, O. *J. Org. Chem.* 1989, 54, 986.

(18) Kanazawa, R.; Tokoroyama, T. *Synthesis*, 1976, 526.

(19) Bal, B. S.; Childers, W. E.; Pinnick, H. W. *Tetrahedron* 1981, 37, 2091.

(20) Sharpless, K. B.; Michaelson, R. C. *J. Am. Chem. Soc.* 1973, 95, 6136.

What is claimed is:

1. A method for the asymmetric synthesis of (+)-pancratistatin, the method comprising:

a) providing an aziridine of the formula:

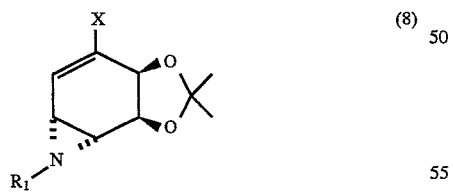

wherein:
X is H or halogen; and
$R_1$ is CBZ or tosyl;

b) adding to the aziridine (8) an amide of the formula:

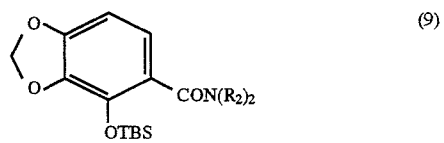

wherein:
$R_2$ is methyl, ethyl or alkyl of C1-C5;
under appropriate conditions to yield an amide of the formula:

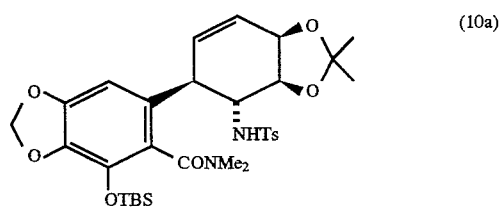

c) acylating the amide product of Step b) with $(BOC)_2O$ to yield a compound of the formula:

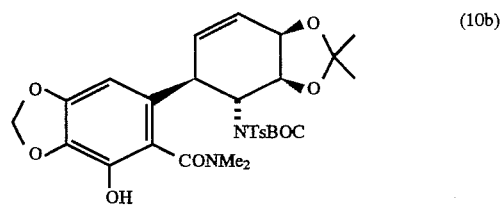

d) detosylating (10b) to yield a dimethylamide of the formula:

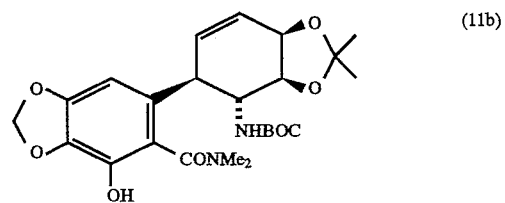

e) reducing the dimethylamide (11b) to yield an aldehyde which can be further converted to a methyl ester of the formula:

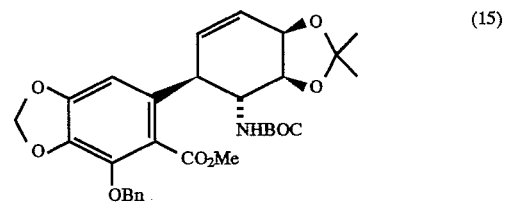

f) deprotecting the methyl ester and subjecting the deprotected compound to epoxidation to yield an epoxide of the formula:

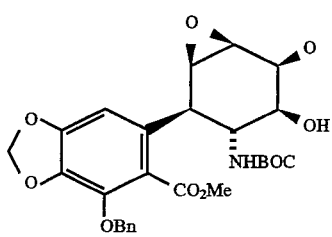

and g) opening the epoxide of Step f) with an appropriate nucleophile to yield pancratistatin (1).

2. A method of claim 1 wherein $R_1$ is tosyl.

3. A method of claim 1 wherein $R_2$ is methyl.

4. A method of claim 1 wherein X is Br or H, $R_1$ is tosyl, and $R_2$ is methyl.

5. A method of claim 1 wherein the amide (9) is added to the aziridine (8) in the presence of s-butyl lithium (s-BuLi) in hexane, tetra methylethylenediamine (TMEDA), tetra hydrofuran (THF), and copper cyanide (CuCN) to form the amide (10a).

6. A method of claim I wherein the amide (10a) in THF is mixed with s-BuLi in hexane, followed by the addition of di-tert-butyl dicarbonate with stirring to yield the amine (10b).

7. A method of claim 1 wherein to a solution of sodium anthracenide is added argon (Ar) and a solution of (10b) to yield (11a) and (11b).

8. A method of claim 1 wherein morpholine-modified sodium bis (2-methoxyethoxy) aluminum hydride in toluene is added with stirring to a solution of (11b) in THF to form the aldehyde of formula (12), (13), (14) or (15).

9. A method of claim 1 wherein the methyl ester 15 is dissolved in a mixture of acetic acid, THF and water with heating to afford methyl-6-[(1R, 4R, 5S, 6R)-6-(tert-butyloxycarbonylamino)-4,5-dihydroxy-2-cyclohexen-1 yl]-4-(phenylmethoxy)-1,3-benzodioxole-5-carboxylate and further adding t-butylhydroperoxide in decane and vanadyl acetylacetonate in benzene with stirring to afford the epoxide (16).

10. A method of claim 1 wherein the epoxide (16) is opened using an appropriate nucleophile such as water in the presence of a catalytic amount of sodium benzoate.

11. A method of claim 1 wherein:

a) the amide (9) is added to the aziridine (8) in the presence of s-butyl lithium (s-BuLi) in hexane, tetra methylethylenediamine (TMEDA), tetra hydrofuran (THF), and copper cyanide (CuCN) to form the amide (10a);

b) the amide (10a) in THF is mixed with s-BuLi in hexane, followed by the addition of di-tert-butyl dicarbonate with stirring to yield the amine (10b);

c) to a solution of sodium anthracenide is added argon (Ar) and a solution of (10b) to yield (11a) and (11b);

d) morpholine-modified sodium bis (2-methoxyethoxy) aluminum hydride in toluene is added with stirring to a solution of (11b) in THF to form the aldehyde of formula (12), (13), (14) or (15);

e) the methyl ester 15 is dissolved in a mixture of acetic acid, THF and water with heating to afford methyl-6-[(1R, 4R, 5S, 6R)-6-(tert-butyloxycarbonylamino)-4,5-dihydroxy-2-cyclohexen-1 yl]-4-(phenylmethoxy)-1,3-benzodioxole-5-carboxylate and further adding t-butylhydroperoxide in decane and vanadyl acetylacetonate in benzene with stirring to afford the epoxide (16); and f) the epoxide (16) is opened using an appropriate nucleophile such as sodium benzoate in water.

* * * * *